(12) United States Patent
Gordon

(10) Patent No.: US 9,144,632 B2
(45) Date of Patent: *Sep. 29, 2015

(54) METHOD FOR PRODUCING STRAIN INDUCED AUSTENITE

(76) Inventor: Richard F. Gordon, Ridgefield, CT (US)

( * ) Notice: Subject to any disclaimer, the term of this patent is extended or adjusted under 35 U.S.C. 154(b) by 1031 days.

This patent is subject to a terminal disclaimer.

(21) Appl. No.: 13/165,928

(22) Filed: Jun. 22, 2011

(65) Prior Publication Data

US 2011/0247731 A1     Oct. 13, 2011

Related U.S. Application Data

(63) Continuation of application No. 11/909,681, filed as application No. PCT/US2006/010544 on Mar. 24, 2006, now Pat. No. 7,988,722.

(60) Provisional application No. 60/846,951, filed on Sep. 25, 2006, provisional application No. 60/665,526, filed on Mar. 25, 2005.

(51) Int. Cl.
  *C22F 1/00* (2006.01)
  *C22F 1/10* (2006.01)
  (Continued)

(52) U.S. Cl.
  CPC ............... *A61L 31/022* (2013.01); *A61L 31/14* (2013.01); *C22F 1/00* (2013.01); *C22F 1/006* (2013.01); *C22F 1/10* (2013.01); *A61L 2400/16* (2013.01)

(58) Field of Classification Search
  CPC ..................... C21D 2201/01; C21D 2211/001; C22C 14/00
  USPC ......... 148/500–511, 563, 668–671, 675–677, 148/707, 402, 409, 410, 419, 421, 426, 148/442; 420/417–421, 441–460, 580
  See application file for complete search history.

(56) References Cited

U.S. PATENT DOCUMENTS

| 4,631,094 A | 12/1986 | Simpson et al. |
| 4,770,725 A | 9/1988 | Simpson et al. |

(Continued)

FOREIGN PATENT DOCUMENTS

| JP | 2000079432 A | 3/2000 |
| WO | WO 95/27092 A | 10/1995 |

OTHER PUBLICATIONS

Xiang-Ming He et al., Study of the $Ni_{41.3}T_{38.7}Nb_{20}$ Wide Transformation Hysteresis Shape Memory Alloy, Metallurgical and Materials Transactions vol. 35A, Sep. 2004, p. 2783-2788.

(Continued)

*Primary Examiner* — Scott Kastler
*Assistant Examiner* — Vanessa Luk
(74) *Attorney, Agent, or Firm* — Handal & Morofsky LLC

(57) ABSTRACT

This disclosure relates to shape memory alloys which have been subjected to a thermal and mechanical treatment to increase the austenite start temperature $A_s \rightarrow A_s'$ such that the shape memory alloy is martensitic at body temperature and when subsequently subjected to a controlled deformation, the shape memory alloy preferentially reverts to the parent phase. One application for this disclosure is a stent for use in a lumen in a human or animal body having a generally tubular body formed from a shape memory alloy which has been subjected to a thermal and mechanical treatment so it deforms as martensite until a critical expansion diameter is reached at which point the tubular body rapidly reverts to the parent phase with much higher mechanical properties. The shape memory alloy comprises Ni—Ti and a ternary element ranging from about 3 at. % to about 20 at. %. The ternary element is effectively insoluble in a Ni—Ti matrix. In a preferred embodiment, the element is selected from the group consisting of niobium, tantalum and zirconium.

11 Claims, 13 Drawing Sheets

(51) Int. Cl.
*A61L 31/02* (2006.01)
*A61L 31/14* (2006.01)

(56) References Cited

U.S. PATENT DOCUMENTS

| | | |
|---|---|---|
| 5,067,957 A | 11/1991 | Jervis |
| 5,876,434 A * | 3/1999 | Flomenblit et al. .......... 623/1.18 |
| 6,053,992 A | 4/2000 | Wu et al. |
| 6,165,292 A | 12/2000 | Abrams et al. |
| 6,312,455 B2 | 11/2001 | Duerig et al. |
| 6,375,458 B1 | 4/2002 | Moorleghem et al. |
| 6,428,634 B1 | 8/2002 | Besselink et al. |
| 6,638,372 B1 | 10/2003 | Abrams et al. |
| 2002/0082681 A1 | 6/2002 | Boylan et al. |
| 2004/0168752 A1 * | 9/2004 | Julien ........................... 148/563 |
| 2006/0212113 A1 | 9/2006 | Shaolian et al. |

OTHER PUBLICATIONS

L. McDonald Schetky, The Application of Constrained Recovery Shape Memory Devices for Connectors, Sealing and Clamping, First International Conferences on Shape Memory and Superelastic Technologies, p. 239-243, copyright 2004.

* cited by examiner

METHOD FOR PRODUCING STRAIN INDUCED AUSTENITE

CROSS REFERENCES TO RELATED APPLICATIONS

This application is a continuation-in-part of U.S. patent application Ser. No. 11/909,681, filed Sep. 25, 2007, now U.S. Pat. No. 7,988,722 B2, issued Aug. 2, 2011, which claims the benefit of U.S. Provisional Application No. 60/846,951, filed Sep. 25, 2006, and PCT/US2006/010555, filed Mar. 24, 2006, which claims the benefit of U.S. Provisional Application No. 60/665,526, filed Mar. 25, 2005, and each of which is incorporated herein by reference in its entirety.

TECHNICAL FIELD

The present disclosure relates to the processing of nickel-titanium (Ni—Ti) ternary alloys and, in particular, to the conditioning of these alloys in a manner that enhances the use of such alloys in medical applications.

BACKGROUND

Metallic engineering materials such as stainless steels, cobalt chromium alloys (Co—Cr alloys) and nickel-titanium alloys (Ni—Ti alloys) are used in variety of medical device applications. One example of a Ni—Ti alloy is NITINOL. The use of these alloys combine mechanical, fatigue, corrosion resistance and biocompatibility properties to create devices useful in a number of medical procedures.

Since the advent of minimally invasive procedures, engineering designers have been trying to work with specific geometries whereby metallic components can be inserted through very small openings in the human body, routed to the desired location and then deployed to a useful size to fulfill the needs of the end application. One such well-known device is a coronary stent, a tubular structure used to hold open blocked or collapsed arteries. The usual method of getting stents into the space is to collapse the metal structure onto a delivery catheter having a sufficiently small overall diameter so it can be routed percutaneously to the coronary artery and expanded to a much larger diameter than the original insertion diameter.

Conventional alloys used in various medical instruments have relied on stainless steel, complex cobalt chrome alloys (such as Elgiloy™ or L605) all of which can have their mechanical properties (i.e. yield strength, ultimate tensile strength break strength, etc) modified through work hardening and annealing. These metals, even with very high yield strength, cannot sustain strains much greater than 0.2 percent (%) without suffering a permanent set. Once a bend or kink has been sustained in a medical instrument or device fabricated from one of the above alloys it is virtually impossible to straighten and remove from the body. For many permanent implants (such as stents), the device may not need to be removed and the permanent deformation may actually be useful to keep the structure in place. However, in the foregoing alloys, Hook's taw dictates that the force to deploy the implant will increase at a linear rate until the material yield point is reached and then the force will continue to increase until the material break point is reached. Additionally, these materials have significant spring back after receiving a significant deformation.

Recently medical device engineers have begun designing metallic components with shape memory alloys. In general, shape memory alloys such as NITINOL having the proper transformation temperature and processing could potentially offer two modes of shape recovery for metallic components inserted into the human body: (1) superelasticity and (2) shape memory recovery.

In the case of superelastic NITINOL the complete "elastic" recovery of strains up to 10% due to stress induced martensite (SIM) can be achieved. When superelastic NITINOL components are subjected to a stress, the strain is accommodated by austenite to martensite crystalline transformation, rather than by the mechanisms that prevail in other alloys such as slip, grain boundary sliding and dislocation motion.

Under typical process condition the stress required to form martensite will be >60,000 pounds per square inch (psi) (414 mega pascals (MPa) and the reverse transformation stress will be >30,000 psi (207 MPa). It can be observed that the reversion stress is lower than the stress at which martensite forms. These stresses are referred to as the upper and lower plateau stresses and their magnitude is dependent on the alloy composition, cold working and thermal treatment that the NITINOL, has received. As the temperature of the specimen is raised, the stress magnitude required to produce SIM is increased; however when the specimen reaches a critical temperature above (the Austenite finish temperature) $A_f$, designated as $M_d$, stress induced martensite cannot be formed, no matter how high the stress. In practical applications, this behavior gives rise to a limitation on using the super-elastic property since it limits the temperature range over which super-elasticity is observed; typically in the binary Ni—Ti alloys, this is a temperature range of about 60° Celsius (C) (108° Fahrenheit) (F), although a 40° C. (72° F.) range is more typical. The desirable temperature range for medical and orthodontic applications is in the region of body temperature, +10° C. to +40"C, can be achieved in these alloys.

Others have applied superelastic NITINOL to medical devices using a 50.8 atomic percent (at. %) nickel/balance titanium formulation which has been cold worked followed by a low temperature anneal to give a combination of shape memory and/or superelastic characteristics. For starting materials having an ingot $A_f$ of 0° C., this processing gives a component with an elastic range of approximately 2% to 8% over a temperature range of +15° C. to +40° C. However, the shortcomings for deployment of a stent application include: (a) the unnecessary bulk of the stent delivery system (since the delivery system must resist the high outward radial force of the compressed stent during shipping, storage and deployment); (b) the high outward radial force of the compressed stent pressing on the inside surface of the delivery sheath can add unwanted friction during deployment of the stent from the sheath; (c) at deployment the rapid stent expansion to its memorized shape can traumatize the vessel wall; and (c) the stent can cause a chronic outward force once deployed that can cause further trauma.

Jervis, U.S. Pat. No. 5,067,957, discloses that a medical device component made from superelastic NITINOL can be externally constrained outside the body via the stress induced martensite mechanism, then placed in the body and de-constrained for deployment.

Duerig, et al., U.S. Pat. No. 6,312,455, discloses a superelastic NITINOL stent for use in a lumen in a human or animal body, having a generally tubular body formed from a shape memory alloy which has been treated so that it exhibits enhanced elastic properties with a point of inflection in the stress-strain curve on loading. This enables the body to be deformed inwardly to a transversely compressed configuration for insertion into the lumen and then revert towards its initial configuration, into contact with and to support the lumen. The shape memory alloy comprises nickel, titanium and from about 3 at. % to about 20 at. %, of the alloy composition, of a ternary element selected from the group consisting of niobium, hafnium, tantalum, tungsten and gold. The ratio of the stress on loading to the stress on unloading at the respective inflection points on the loading and unloading curves is at least about 2.5:1, and the difference between the stresses on loading and unloading at the inflection points is at least about 250 MPa.

Besselink, et al., U.S. Pat. No. 6,428,634, discloses a method of processing a highly elastic stent made from a Ni—Ti—Nb based alloy which contains from about 4 to about 14 at. % Nb and in which the atomic percent ratio Ni to Ti is from about 3.8 to 1.2, comprising working the alloy sufficiently to impart a textured structure to the alloy, at a temperature below the recrystallization temperature of the alloy. Preferably, the alloy is worked at least 10%, by a technique such as rolling or drawing, or another technique which produces a similar crystal structure. The alloy has increased stiffness compared with Ni—Ti binary alloys with superelastic properties.

For the case of shape memory recovery mentioned earlier, the thermoelastic shape memory alloys can change from martensite to austenite and back again on heating and cooling over a very small temperature range, typically from 18° C. to 55° C. On cooling from the austenitic phase, often called the parent phase, martensite starts to form at a temperature designated as $M_s$ (martensite start) and upon reaching the tower temperature, $M_f$ (martensite finish), the alloy is completely martensitic. Upon heating from below the $M_f$ temperature the martensite starts to revert to the austenitic structure at $A_s$, and when the temperature designated as $A_f$ is reached, the alloy is completely austenitic. These two crystalline phases have very different mechanical properties: the Young's Modulus of austenite is $12 \times 10^6$ psi (82,728 MPa), while that for martensite is about $4 \times 10^6$ psi (27576 MPa); and the yield strength, which depends on the amount of cold work the alloy is given, ranges from 28 to 100 thousand pound per square inch (ksi) (193 to 689 MPa) for austenite and from 10 to 20 ksi (68 to 138 MPa) for martensite.

Additionally, a NITINOL structure processed to exhibit shape memory and deformed in the martensitic state can recover up to 8% strain on heating to austenite. This would be an extremely handy way to deploy devices or recover accidental bending and kinking of devices in the human body if it were not for the heating and cooling extremes that must be achieved.

Simpson, et al., U.S. Pat. No. 4,770,725, discloses a Ni—Ti—Nb shape memory alloy and article, wherein niobium varies from about 2.5 to 30 at. %. Also disclosed is an article made from these nickel/titanium/niobium alloys.

Simpson, et al., U.S. Pat. No. 4,631,094, discloses a method of processing a nickel/titanium-based shape memory alloy. The method comprises over deforming the alloy so as to cause at least some amount of non-recoverable strain, temporarily expanding the transformation hysteresis by raising the austenite transformation temperature, removing the applied stress and then storing the alloy at a temperature less than the new austenite transition temperature. Simpson also discloses an article produced from this method.

Wu, et al., U.S. Pat. No. 6,053,992, discloses a mechanism that uses the shape recovery of a shape memory alloy for sealing openings or high-pressure passages. A component made of a shape memory alloy can be processed in its martensitic state to have a reduced dimension smaller than that of the opening or the passage to be sealed. Upon heating, shape recovery takes place that is associated with the reverse crystalline phase transformation of martensite. The shape recovery of the previously processed shape memory alloy component yields a diameter greater than that of the opening or passage to be sealed. The shape recovery provides the dimensional interference and force required for sealing.

Wu, et al., builds on the work of Simpson, et al., U.S. Pat. No. 4,770,725, to use both the defined chemistry and the specified process method to effect a specific heat sealing application which employs a heat activated recovery transformation.

The wide thermal hysteresis available from thermal and mechanical treatment of alloys disclosed in the literature is attractive for articles which make use of a thermally induced configuration change, since it enables an article to be stored in the deformed configuration in the martensite phase, at the same temperature at which it will then be in use, in the austenite phase. This thermal and mechanical treatment is used in a variety of industrial heat—to recover couplings and connectors (L. Mcd. Schetky, The Applications of Constrained Recovery Shape Memory Devices for Connectors, Sealing and Clamping, Proceedings Super-elastic Technologies, Pacific Grove, Calif. (1994)).

It has been reported that a reverse transformation start temperature $A_s'$ has been raised to +70° C. after specimens were deformed to 16% strain at different temperatures, where the initial states of the specimens were pure austenite phase and/or martensite phase depending upon the pre-straining temperature regime. It was found that a transformation hysteresis width of 200° C. could be attained and the reverse transformation temperatures were measured by forcing a shape-memory recovery via heating, and that up to 50% of the pre-strain could be recovered. The work was done by Xiang-Ming He, et, al, Study of the $Ni_{41.3}Ti_{38.7}Nb_{20}$ Wide Transformation Hysteresis Shape Memory Alloy, Metallurgical and Materials Transactions, Vol. 35A, September 2004. The work cited is an optimization of various pre-straining conditions to maximize the strain recovery possible for heat recovery application.

While the wide hysteresis confers certain advantages when the thermally induced changes in configuration are to be exploited, a wide hysteresis in stress-strain behavior is generally inconsistent with the properties of an alloy that are desirable in stent or medical device applications.

Various methods have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using other stents involved maintaining the radial rigidity needed to hold open a body lumen while at the same time maintaining the longitudinal flexibility of the stent to facilitate its delivery.

What has been needed and heretofore unavailable is a stent which has a high degree of flexibility so that it can be advanced through tortuous passageways, can be readily expanded, and yet have the mechanical strength to hold open the body lumen into which it expanded.

Thus, it is desirable to develop an alloy that is very ductile and uniquely suited for deployment of medical devices, such as stents, into the human body. In particular, for stents, it is desirable that the compressed stent maintain its shape until expanded.

SUMMARY

In one embodiment; the present disclosure provides a Ni—Ti ternary alloy that is particularly useful for medical instruments and devices, as well as components thereof.

In another embodiment, the present disclosure provides an alloy having variable hardness/stiffness properties and which is useful for medical instruments and devices, as well as components thereof.

In yet another embodiment, the present disclosure provides a material for making medical instruments and devices as well as components thereof that are formable without crack initiation sites when expanded or deformed.

Another embodiment is directed to a method of producing a Ni—Ti ternary shape memory alloy, specifically strained induced austenite (SIA), with improved characteristics which are desirable for use in various applications such as medical devices.

The disclosure provides for a stress induced martensite that is locked place by the presence of a third element such that $A_s'>37°$ C. The material can be placed inside a mammalian body that can have its $A_s' \rightarrow A_s$ by controlled deformation, thus creating a material having mechanical properties superior to the mechanical properties upon insertion. When the material is used in a medical device structure, the device can be placed inside a mammalian body and restored to a stiffer mechanical state after controlled deformation or expansion.

The material is particularly advantageous in that a medical device comprising the material can be placed inside a mammalian body that can have its $A_s'$ initially reduced to a temperature <37° C. by controlled deformation, and further restoration of the original $A_s$ and austenitic transformation of mechanical properties by heat driven shape memory recovery process. Once placed inside a mammalian body, the material can be restored to a stiffer mechanical state after controlled deformation whereby $A_s'<37°$ C., and the austenitic transformation is completed by a combination of controlled deformation and assisted by temperature driven shape memory recovery process.

The disclosure is also directed to a method for the thermal mechanical treatment of a Ni—Ti alloy performed at temperatures $<M_d$ (the temperature at which martensite can no longer be stress induced) where the hysteresis is widened such that after the treatment is completed $A_s<A_s'$, or when used for medical applications, $A_s<37°$ C.$<A_s'$.

The present disclosure provides a method of producing a Ni—Ti ternary alloy that exhibits properties desirable for medical instruments and devices. In particular, the treated alloy exhibits a high degree of ductility and low mechanical strength properties during insertion into the body and subsequently can be made stiff with significantly higher mechanical properties after being subjected to a controlled deformation of a critical magnitude.

The present disclosure is directed to a method for the thermal mechanical treatment of a Ni—Ti ternary alloy performed at temperatures $<M_d$ wherein the hysteresis is widened such that after the treatment is completed $A_s<A_s'$, comprising:
  a) annealing or partially annealing a Ni—Ti ternary alloy through a high temperature solution treatment followed by cooling;
  b) mechanically straining the alloy be under a load while simultaneously cooling the material to a temperature around or less than $M_s$, thus shifting $A_s$ up much higher such that $A_s<A_s'$ and retaining a sufficient amount of strain in the strained element whereby if controlled deformation is applied the alloy is transformed to the austenitic phase, shifting $A_s'$ to $A_s$.

In preferred embodiments, the alloy is mechanically strained between about 10 to about 25% under a constant load while simultaneously cooling the material to a temperature around or less than $M_s$, thus shifting $A_s$ up much higher such that $A_s<A_s'$ and retaining about 2% to about 15% strain in the strained element whereby if controlled deformation is applied the alloy is transformed to the austenitic phase, shifting $A_s'$ to $A_s$.

Mechanical straining of the alloy during cooling forms martensite variants having volume fractions comprised mainly of (a) stress induced martensite and or (h) twinned and deformed martensite. The volume fractions formed are dependent upon the cooling rate and the applied pre-strain load stress. For instance if the applied pre-strain is at a temperature $>A_f$ and $<M_d$, the microstructure may reveal formation of stress induced martensite and if the pre-strain is applied at a temperature $<A_f$ the micro structure may reveal formation of twinned and deformed martensite. Optimization of the martensite volume fractions are dependent upon the process pre-straining conditions and temperature. Reorientation of the martensite variants are prevented by the presence of a third insoluble element in the metal matrix giving rise to $A_f'$.

Controlled deformation is displacement and the associated stress/strain field (bending, compression, tension, shear) required to initiate a complete or partially complete transformation wherein $A_s'$ is shifted back to $A_s$. During controlled deformation the prepared material is deformed easily at low stress levels, and after a sufficient range of displacements have been completed, the material undergoes a permanent shift in mechanical properties such that further displacement now occurs at higher stress levels.

By pre-straining the Ni—Ti ternary alloy using the method described above, it has been found possible to produce a shift of a normally austenitic alloy at body temperature, into an alloy that has martensitic properties at body temperature.

Surprisingly, the controlled deformation causes the pre-strained material to become much stiffer where there appears to be almost a spontaneous conversion from martensite to austenite. The controlled deformation appears to "unlock" the martensitic alloy structure and cause the mechanical properties to revert seemingly spontaneously back to the austenitic alloy. Adding controlled deformation in the appropriate amount will cause the $A_s'$ to be restored to the original material $A_s$. In certain embodiments of the disclosure, the controlled deformation may occur through bending, compression, tension and/or shear stresses.

The resulting material is martensitic at all temperatures $<A_s'$, very ductile and uniquely suited for deployment of medical devices such as stents into the human body. After pre-straining the material, the compressed stent maintains its shape until balloon expanded.

In one aspect of the disclosure, the shape memory alloys processed by the method comprise a ternary element E from 3 at. % to about 20 at. % of the alloy composition E can comprises a ternary element that is effectively insoluble in the Ni—Ti matrix such as Nb, Ta or Zr, and the like.

The pre-straining process, in combination with the preferred Ni—Ti alloy composition employed renders the components flexible that, in turn, make medical components, in particular stents, easy to insert and deliver into the desired location. The resulting alloy is a material that can revert from martensite to austenite by deformation process as described above in (b). This characteristic is particularly advantageous when trying to create a structure in the human body because delivery can be through a small opening and then after deployment the structure takes on the stiffer rigid property.

BRIEF DESCRIPTION OF THE DRAWINGS

The foregoing and other Objects and features of the disclosure will become apparent from the following description of preferred embodiments of the disclosure with reference to the accompanying drawings, in which.

DETAILED DESCRIPTION OF THE ILLUSTRATIVE EMBODIMENTS

Most stents on the market today are made from materials such as 316L or Co Cr (L605 and MP35N) materials. The stents are compressed, permanently deformed and crimped onto a delivery catheter equipped with an underlying balloon. Once positioned in the lumen, a balloon is inflated to outwardly expand the stent material beyond its yield point, until the stent makes contact with the vessel wall.

Figure 1:
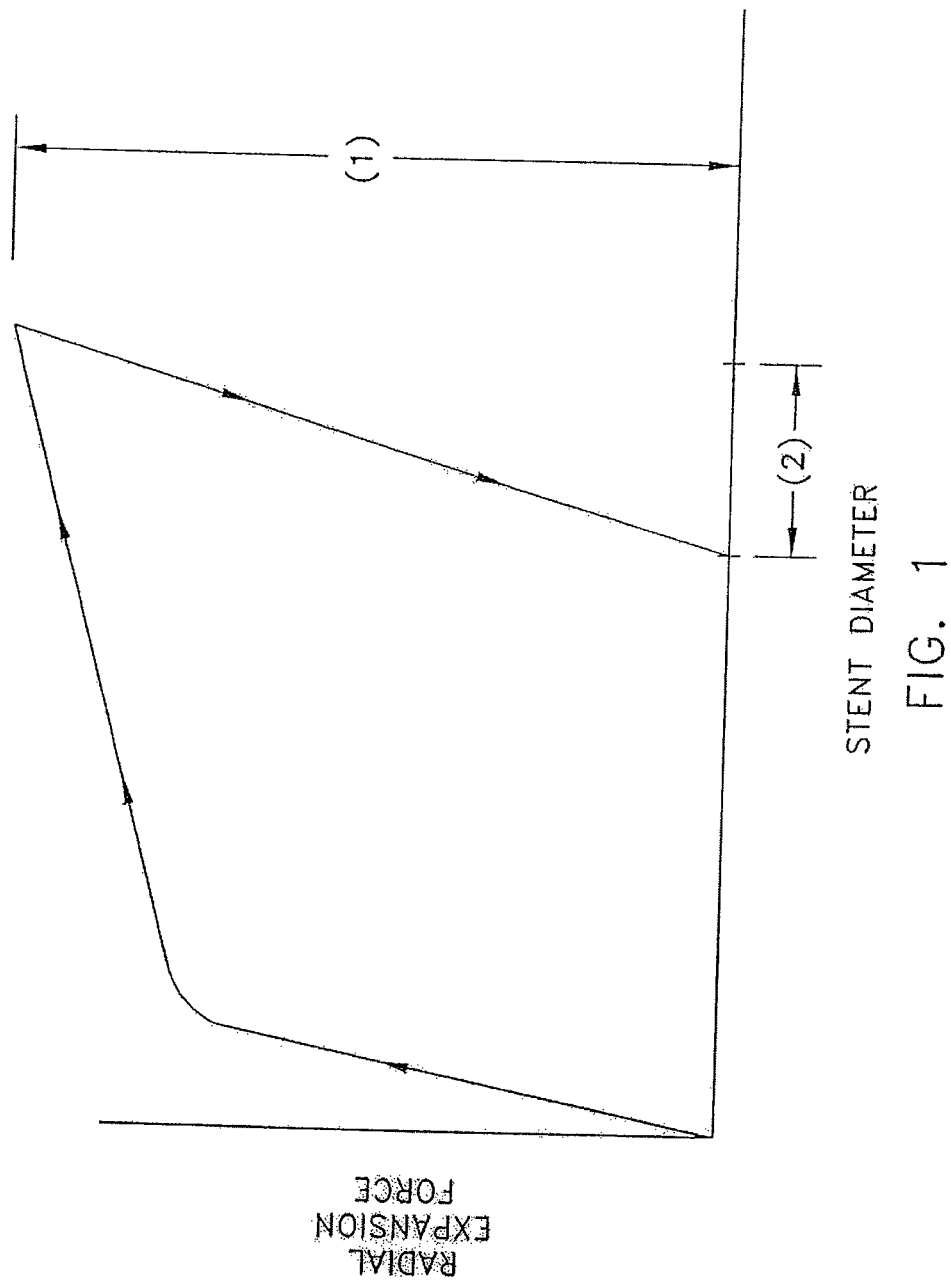
FIG. 1 is a graph showing radial expansion force versus stent diameter for a 316L or Co—Cr annealed stent material.

FIG. 1 shows how the radial expansion force varies as a function of stent diameter. These stent materials have four limitations: (1) the expansion force increases with expansion diameter (FIG. 1); (2) material spring back requires (FIG. 1) over expansion to achieve the final diameter and this results in vessel trauma; (3) the high force to expand the stent requires an inflation balloon to be of a heavy wall thickness increasing the overall profile and stiffness of the delivery system; and (4) under X-Ray fluoroscopy some of the above mentioned materials have poor visibility.

Additionally, some stents on the market today are made from superelastic NITINOL. In these devices, the "active" $A_f$ (as defined by ASTM F2082) of the final stent structure is between 0° C. and 37° C., more particularly between 10° C. and 25° C. These stents are radially compressed at (a) room temperature against a radial outward force generated by the upper plateau stress (about 70 ksi or 483 MPa) of superelastic NITINOL or (b) at a temperature below $M_s$ against the mechanical stress (about 12 ksi or 83 MPa) of martensite. In either case, at room temperature the outward radial force of the compressed stent diameter can be constrained with a delivery sheath fitting over the compressed stent. These stent materials have the following limitations: (1) the constrained outward force of the stent requires an outer sheath which adds unwanted stiffness and bulk to the delivery system; (2) the continually outward force of the compressed stent exerts a frictional force on the sheath which increases the sheath retraction force; (3) once the sheath is pulled back the stent rapidly expands to the final diameter which may cause vessel trauma; (4) the stent diameter cannot be over expanded to accommodate any gap between the vessel lumen and the selected stent; and (5) under X-Ray fluoroscopy, binary NITINOL has poor visibility.

In one aspect of the disclosure, the shape memory alloys processed by the method comprise a ternary element E from 3 at. % to about 20 at. % of the alloy composition, wherein E can comprise a ternary element that is effectively insoluble in the Ni—Ti matrix. Examples of suitable ternary elements include, but are not limited to, niobium (Nb), tantalum (Ta), Zirconium (Zr) and the like. It is also thought that shape memory alloys comprising combinations of element E can be effective.

TABLE I

Composition of Materials Suitable for "Strain Induced Austenite"

| Alloy Composition | Titanium (Atomic %) | Nickel (Atomic %) | E (Atomic %) |
|---|---|---|---|
| Ni—Ti-E | Y % | Z % | 0.1 < X % < 20% |

1. X is the percentage addition of a third insoluble element (E) such as Niobium (Nb), Tantalum (Ta) and other insoluble ternary elements into the Nickel Titanium matrix. The element is supplied in sufficient amounts to optimize the "locking and unlocking" mechanism of "strain induced austenite."
2. Y and Z are used to adjust the ratio of Nickel and Titanium necessary to achieve the target ingot $A_s$ temperature considered optimal by the end application. The ratio of Atomic Percent Ni to Atomic Percent Ti is from about 1.6 to .60.

In particular, the insoluble ternary element (Nb, Ta, or Zr) appears to play a role to "lock" the $A_s'$ structure during the pre-straining cycle in such a way that restoration of the austenite state is prevented until either (a) the materials is heated above $A_s'$ and shape recovery takes place or (b) the controlled deformation sets up a strain field sufficient to trigger material "unlocking" and restoration of original material.

In contrast with other materials, the alloy of present disclosure is particularly well suited for structures that are packed in a small configuration, easily expanded with minimal force, and later after deployment becomes significantly stiffer, a property that is desired for various medical components, particularly stents.

Example 1

Preparation of the Pre-Strained Alloy

Figure 2:
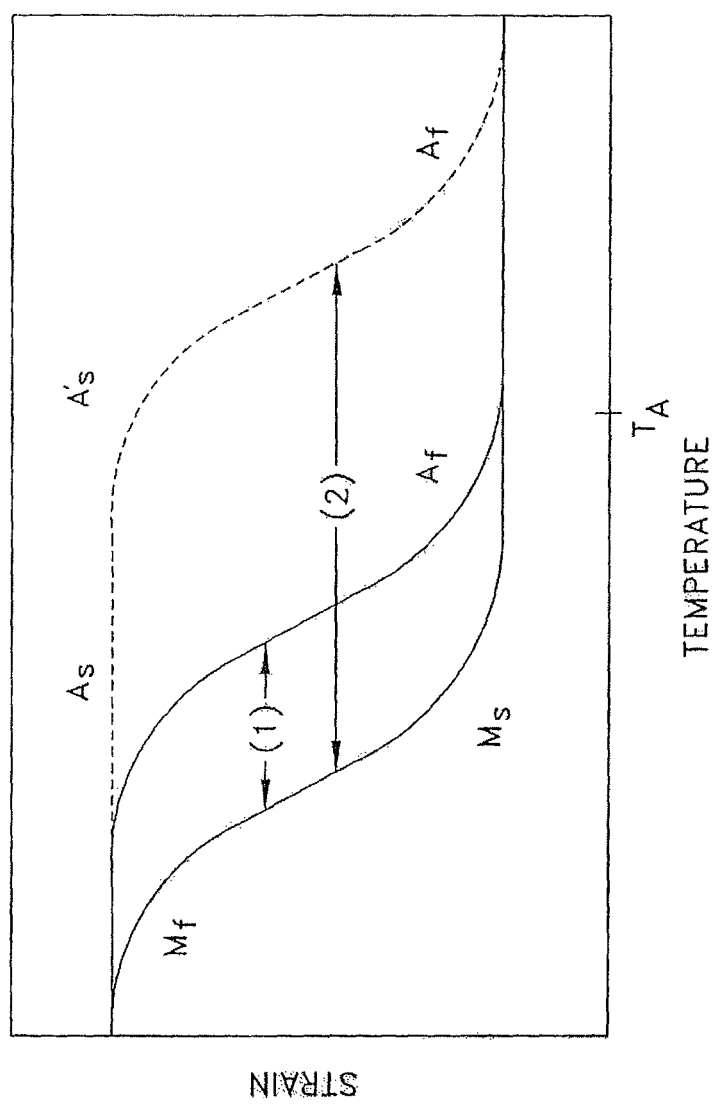
FIG. 2 is a graph of temperature vs. strain showing the shift of $A_s \rightarrow A_s'$ after an alloy material [1] has been processed by the first part of method while [2] is an example of an alloy according to the present disclosure, processed by the method.

The method was applied to $Ni_{44}T_{47}Nb_9$ alloy to provide the response illustrated in FIG. 2 which showed an increase of $A_s \to A_s'$ and the widening of the hysteresis from [1] to [2]. The alloy was partially or fully annealed between 450° C. to 900° C., particularly 650° C. to 900° C. for <60 minutes wherein after cooling the austenite start temperature $A_s$ was about −65° C. The material was strained under load while the material was cooled, preferably to a temperature between the martensitic start temperature of $M_s$ about −85° C. and the $A_s$ about −65° C. The material was then strained 8% to 25%. Upon completion of the pre-straining cycle $A_s'$ was elevated above 37° C. and particularly above 60° C.

Another aspect of the disclosure is the effective insolubility of niobium in the Ni—Ti matrix. It appears that during the treatment method, there is a partitioning of the total strain of the material and each component (i.e. nickel-titanium and beta niobium) seems to work as an individual component at similar levels of flow stress. Depending upon the pre-straining temperature regime, martensitic Ni—Ti deforms reversibly by either twin boundary motion or stress induced martensite motion, while the beta-niobium deforms irreversibly via slip to "lock" the martensitic deformations in place. In either case the locked structure mechanism corresponds to the new $A_s'$.

After treatment, the Ni—Ti—Nb microstructure is comprised of: (a) stress induced twined martensite consisting of type I (111) M twins and occasionally (001) M twins and anti-phase domain boundaries (Icomet-92); and (b) the soft beta-niobium particles are deformed irreversibly via slip.

The plentiful block shaped niobium phases are adjacent to the different martensite variant boundary below $M_s$. After pre-straining, these block phases serve as obstacle sources to inhibit the reorientation of the martensite, so martensite reorientation has difficulty proceeding at lower stress levels. When stress is added by controlled deformation (e.g., bending), the martensite reorientation is free to proceed once the blocking constraint of the niobium phases is removed by the additional stress.

Another aspect of the method is the creation of expandable structures that can be collapsed and ready for small opening insertion, that do not required external constraints. In this way, the pre-strained structure is comprised of (a) stress induced martensite or (b) twinned and deformed martensite which is "locked" in place by the present of the third and insoluble element (in this case the soft niobium particles). This type of structural element may not need an external cover to hold back the restoring force typically found in superelastic NITINOL expandable structures. One advantage to the method is that no external cover is required for insertion, leading to a reduced design profile that is advantageous for a number of medical device applications.

A tubular stent element can be manufactured by one of the following series (e.g., 1, 2 or 3) of process steps. Note that the thermal mechanical treatment can occur either before or after the machining step in items 1 and 2 below.

1) Starting Tube—Laser or Chemical Machining—Pre-Straining to increase $A_s'$—Deployment and Expansion 2) Starting Tube—Pre-Straining to Increase $A_s'$—Laser or Chemical Machining—Deployment and Expansion 3) Starting Wire—Shape Setting—Pre-straining to Increase $A_s'$—Deployment and Expansion Other appropriate manufacturing methods incorporating the treatment method would be known to those skilled in the art for use in applications with wire, tube, strip or appropriate forms.

As discussed above, the present disclosure offers an alternate method to deploy structures and devices in the human body that are made from other materials (i.e. 316L and Co—Cr alloy systems) and super elastic NITINOL.

When the pre-strained $Ni_{44}Ti_{47}Nb_9$ material is heated such that $T > A_s'$, the Ni—Ti matrix reverts to its parent phase (Table 1—Process I) with a corresponding increase of mechanical properties (FIG. 3—Process I) sufficient to overcome the "locking" force of the deformed beta niobium particles and thereby "unlocking" the structure and recovering both the original pre-strained shape and austenite start temperature ($A_s$). The drawback to the resulting material is that heating is not a preferred method to deploy a medical device into a mammalian body.

TABLE I

Illustrates the Process Differences Between Process I (Heating) and Process II (Controlled Deformation) which is Strain Induced Austenite for $Ni_{44}Ti_{47}Nb_9$.

| Process Method | Initial Preparation | Pre-Straining | Application | Recovery Phase |
| --- | --- | --- | --- | --- |
| I | Cold Working plus Annealing @ 450 to 850° C. 1 to 30 minutes | Pre-strain while cooling article to about $M_s$ or $< M_s$ temperature to achieve: $A_s \to A_s'$ | Constrained Recovery Application (e.g. pipe coupling) | Heating $T > A_s'$ To achieve: $A_s' \to A_s$ and shape recovery |
| II | Cold Working plus Annealing 450 to 850° C. 1 to 30 minutes | Pre-strain while cooling article to about $M_s$ or $< M_s$ temperature to achieve: $A_s \to A_s'$ | Biomedical Device Insertion (e.g. stent) | Controlled deformation of sufficient scale to achieve: $A_s' \to A_s$ | in the present method, the pre-strained material is "unlocked" by a controlled deformation (Table 1 Process II) and upon reaching a critical strain level ($\epsilon_c$) (FIG. 3—Process II), the soft martensitic structure begins to revert to the parent phase having improved mechanical properties useful in many medical devices including stents.

Figure 3B:
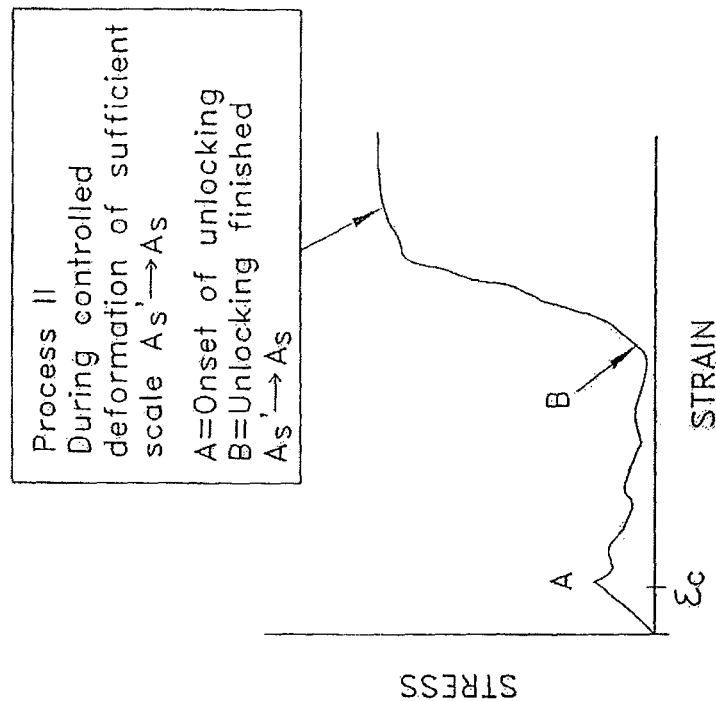
FIGS. 3a and 3b shows two graphs comparing pre-strained Ni—Ti-E alloy heating (I) and deformation (II) recovery modes.
Figure 3A:
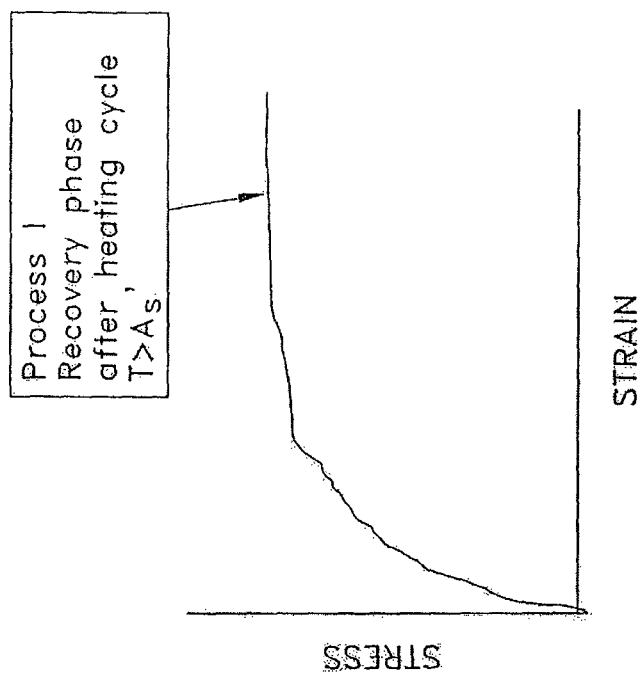

Specifically, a controlled deformation of sufficient strain ($\epsilon_c$) can cause the parent phase to preferentially nucleate in a jump-like manner. At locations where flow stress levels are sufficiently large, soft niobium particles no longer constrain martensite variants which are now "unlocked" an undergo a parent phase transformation as a series of stress level reductions (FIG. 3—Process II).

Example 2

Three Point Bend Test

Figure 4:
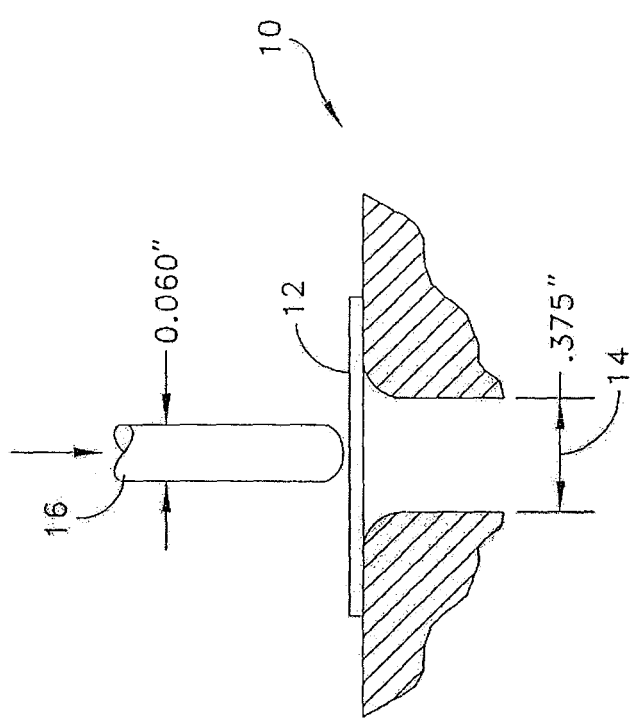
FIG. 4 is a schematic representation of an apparatus used to perform a three point bend test to show the onset of "unlocking" mechanism.
Figure 5:
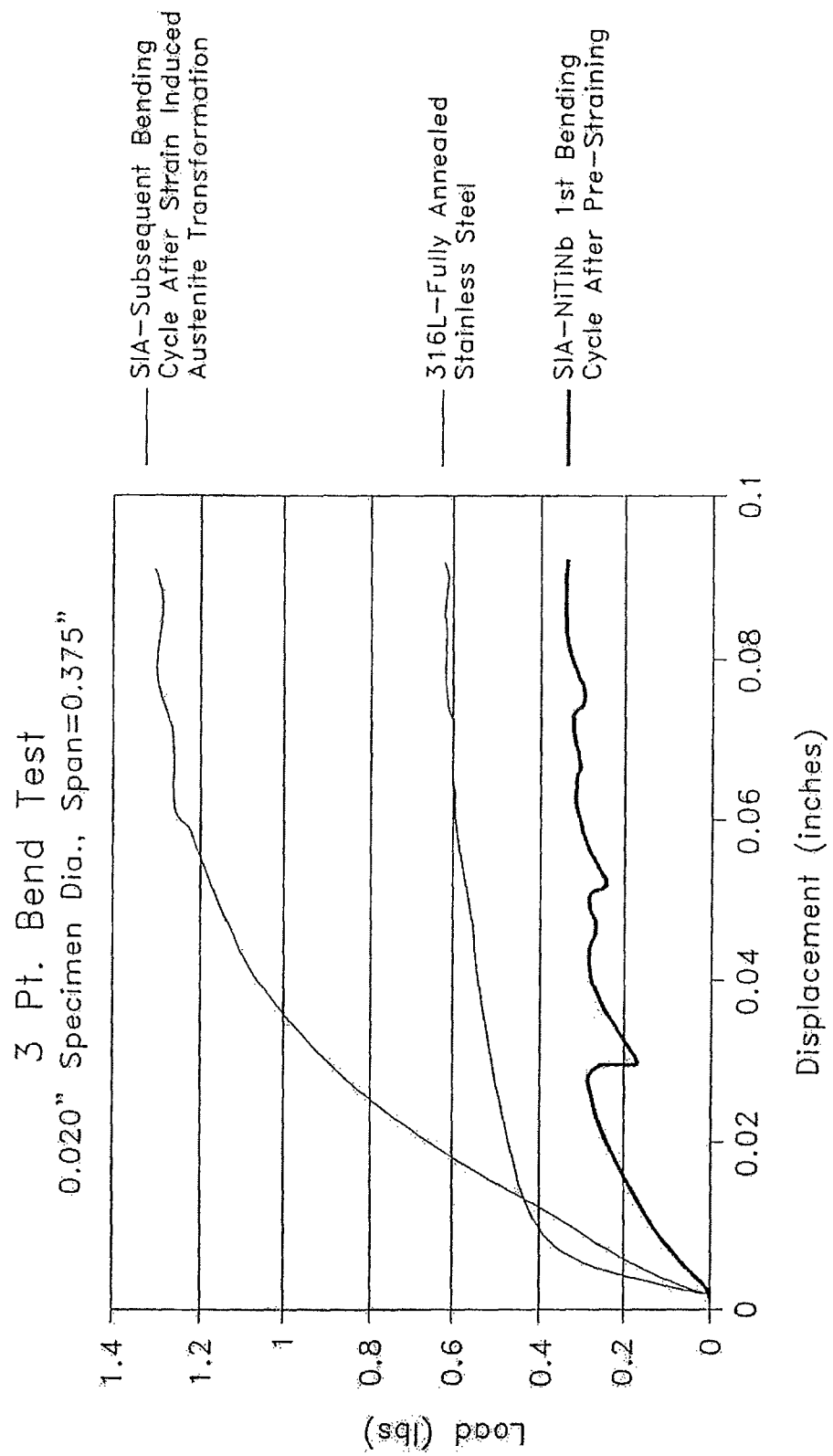
FIG. 5 is a graph of a three point bend test performed with the apparatus of FIG. 4. These plots show first and second bending cycles of strain induced austenite and the unloading and reloading which occur at 0.060 thousandths (") (0.1524 centimeter (cm) displacement giving some indication of the spring back characteristic.

Referring to FIGS. 4 and 5, a three point bend test was performed to demonstrate the "unlocking" clicking phenomena, the spring back characteristic in the "unlocking region" at 0.060" (0.15 cm) displacement, and to show the stiffness transformation between the first and second bend cycle.

A 0.020" (0.05 cm) 316LVM (low carbon vacuum melted) wire in the fully annealed condition (typical of condition and chemistry for stent material) was prepared.

For the Strain Induced Austenite (SIA), 0.020" (0.05 cm) Ni—Ti—Nb was pre-strained under approximately 302 ksi (2082 MPa) during a cooling cycle from 20° C. to −140° C. The wire had about 10% retained strain after returning to room temperature.

A test apparatus 10 for the above method is shown in FIG. 4 below. Wire specimen 12 was placed across a 0.375" (0.952 cm) unsupported span 14. An Instron 5544 equipped with a 20 pound (lb.) (9.072 kilogram (kg)) load cell and Blue Hill software was used for data capture. Anvil 16 was secured in the Instron cross head and (a) advanced down at 0.04"/minute (0.10 cm/min) for a distance of 0.060" (0.15 cm) (b) moved upward until the load reached zero, and (c) advanced down until total displacement equaled 0.100" (0.254 cm).

FIG. 5 shows the load displacement behavior for 0.020" (0.05 cm) SIA wire 12, subsequent bending cycle after a strain induced austenitic transformation and a 316LVM fully annealed wire of equivalent cross section. The "unlocking mechanism" of the SIA material 12 was apparent in the displacement range from about 0.03" (0.076 cm) to 0.08" (0.2032 cm). The onset of material "unlocking" occurred at 0.03" (076 cm) and the load capacity was suddenly shifted from 0.28 lbs (127 grams (g)) to 0.16 lbs (72 g). There were a number of other small drops in load capacity observed up to 0.080" (0.203 cm) of displacement. The net effect of the unlocking mechanism is that bend force for the SIA material did not grow very large. In comparison, the performance of 316L fully annealed material (with well documented extremely low stiffness and ductile material properties) was perhaps stiffer by a factor of two throughout the range of displacement.

At 0.060" (0.15 cm) wire 12 was unloaded to zero and then the load was reapplied. The spring back for the SIA material was about 0.015" (0.038 cm) and the 316LVM fully annealed material was about 0.009" (0.0229 cm). The test was stopped at 0.93" (2.36 cm) of displacement. The peak force for SIA was 0.33 lbs (0.15 kg) while the peak force for 316LVM was 0.62 lbs (0.28 kg). The data demonstrates that: (a) the initial bending stiffness of SIA is about one-half (½) that of annealed 316 LVM, (b) the "unlocking" phenomena is prevalent in the range between 0.03" (0.0762 cm) and 0.08" (0.203 cm) of displacement and is responsible for keeping the stiffness extremely low during initial bending. In addition, it is well documented that fully annealed 316LVM has yield strength of approximately 45,000 psi (310 MPa), whereas the first bend cycle of SIA material has a yield point considerably less than the 316LVM.

After the initial bending cycle the deformed SIA wire 12 was straightened and retested under the same 3 point bend test conditions. These results are shown in FIG. 5 and identified as SIA—Subsequent Bend Cycle. At about 0.06" of deflection the subsequent bending cycle after strain induced austenitic transformation showed a wire 12 that was more than twice as stiff as the 0.020" 316LVM fully annealed wire and more than 4 times stiffer than the 0.020" SIA wire during the first bending cycle. This is evidence of the bending induced transformation from martensite to austenite.

Example 3

Observation of the Reverse Phase Transformation by Simple Bending

Further evidence of strain induced austenite was easily observed using wires having a starting diameter of 0.020" which, after the pre-straining sequence described above, resulted in stable martensite material having a diameter of 0.0192". As described above, there are two paths by which the original 0.020" wire diameter can be recovered: (1) by simple bending and (2) by heating. The heat to recovery method for these alloys has been successfully employed for industrial applications but is not considered acceptable for medical applications because of the high temperature (e.g., greater than 60° C.) required to effect the transformation. However, if the pre-strained wire is bent between ones fingers at room temperature, the transformation taking place can be observed by a soft clicking action that ends in a stiff bent wire. If the bent wire is now straightened by bending in the opposite direction more soft clicking can be observed. The end result is a phase transformation of wire from a soft martensitic material into a stiffer austenitic material. Proof that a reverse transformation has taken place can be found by measuring wire diameter with calipers. After bending the pre-strained wire as described above, wire recovered in diameter from 0.0192" after pre-straining, to its original 0.020" diameter. This growth in wire diameter is proof of the recovery transformation via bending.

Example 4

Acculine Bend Moment Testing

Figure 6:
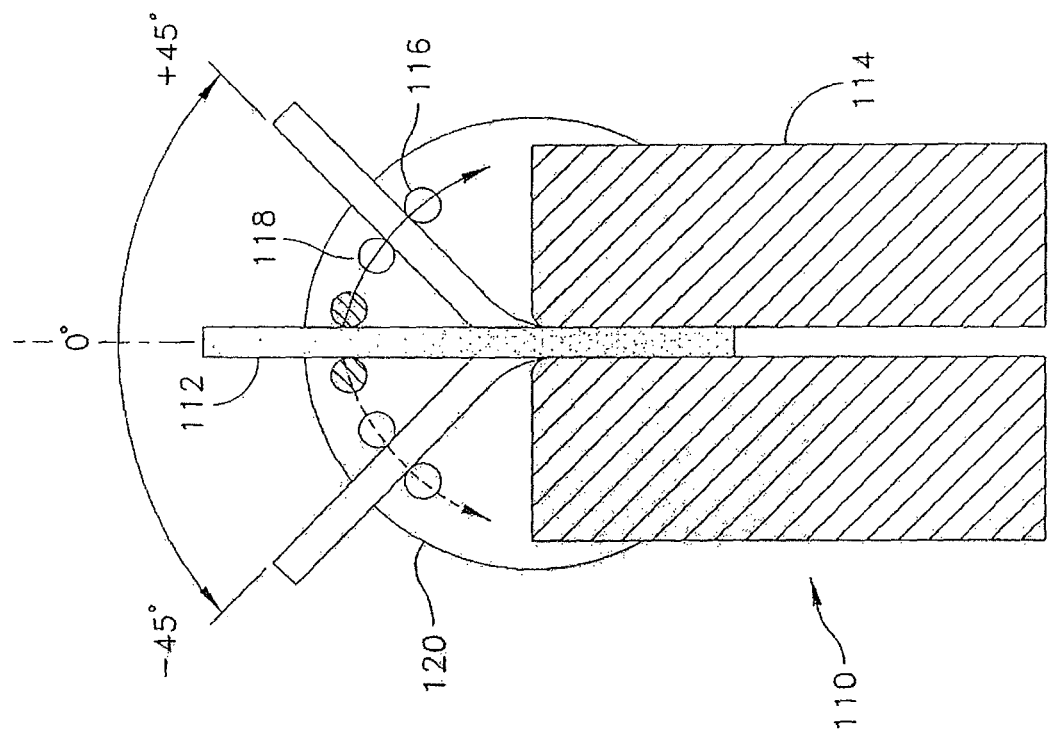
FIG. 6 is a schematic representation of some components used in the Acculine bend moment tester used to provide cyclic bend testing with a constant moment arm.
Figure 7:
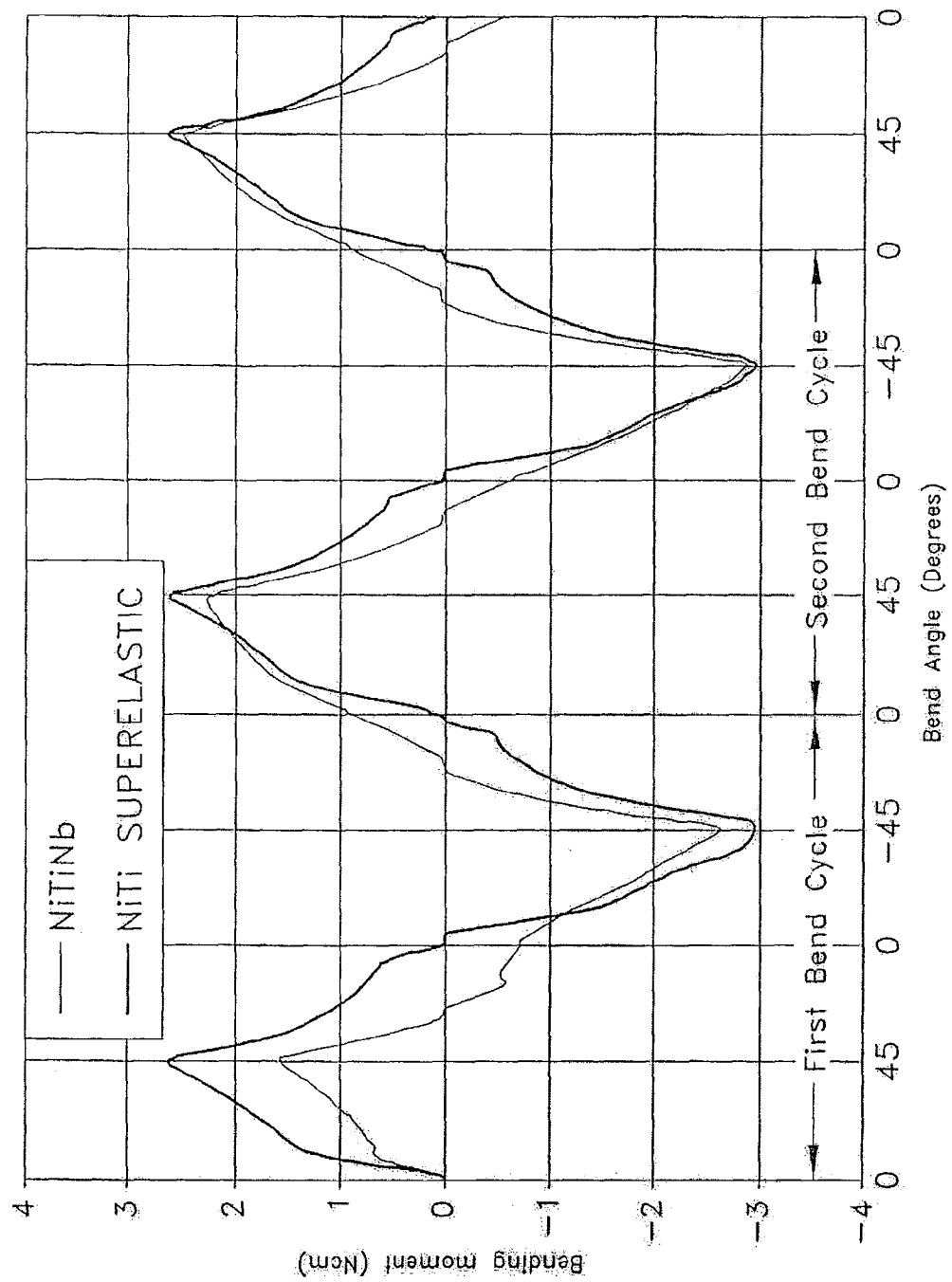
FIG. 7 is a graph of the test results of the tests run with the apparatus of FIG. 6 showing strain induced austenite undergoing stiffness transformation during its first and second bending cycle.

Referring to FIGS. 6 and 7, this test compared the bending moment transformation behavior of 0.020" pre-strained Ni—Ti—Nb as described above and 0.020" superelastic straight binary NITINOL. The bending stiffness of strain induced austenite and superelastic NITINOL straight wire samples were tested under identical conditions using an Acculine AE#-BM Bend Tester 110. Each 0.020" wire specimen 112 was mounted between custom mounting blocks 114 with a 1 millimeter (mm) bend radius. Drive pins 116 and 118 rotated at 9.0 degrees per second (°/sec) to maintain a constant 0.3 cm moment arm while wire 112 was deflected from the vertical position 0°) counter clockwise to +45°, returned to 0°, counter clockwise to −45° and back to 0° to complete one bend cycle. Data was collected by a 10 in-oz rotary torque measurement sensors 120 and 122 and captured for graphical Microsoft Excel presentation. FIG. 6 shows the experimental set up. FIG. 7 is a graph of the data from the first, second and third bend cycle. The first bend cycle shows a peak moment for the Ni—Ti—Nb to be about 41% less then superelastic NITINOL, the second bend cycle shows the peak maximum bend moment to be about 13% of the peak moment of superelastic NITINOL, and the third cycle shows the Ni—Ti—Nb is approaching the performance of the superelastic NITINOL wire. This is further evidence that pre-strained Ni—Ti—Nb had undergone a transformation from a locked NITINOL structure ($A_f^t$) to an unlocked structure restoring the original $A_f$.

Example 5

Expansion of Two Parallel Wires

Figure 8:
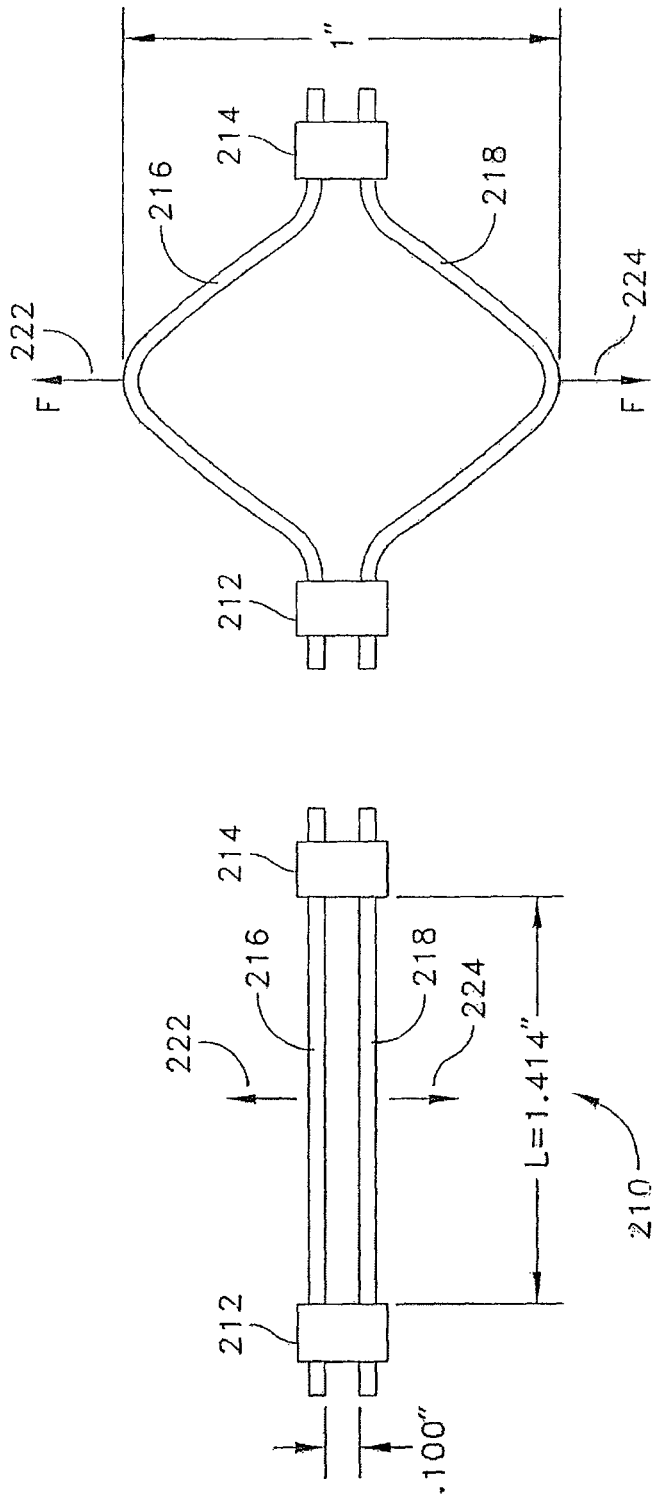
FIG. 8 is an apparatus to measure of the generic stent cell performance characteristic.
Figure 9:
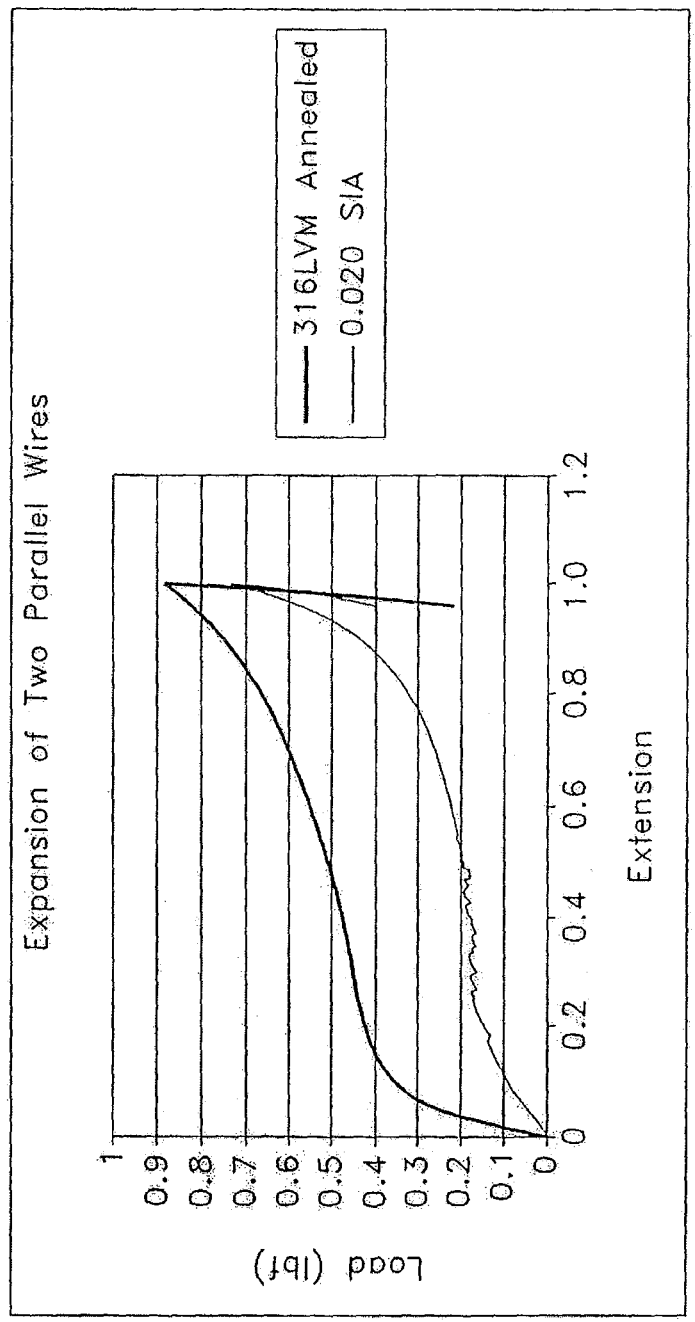
FIG. 9 is a graph of data of the test using the apparatus of FIG. 8.
Figures 10A, 10B, 10C:
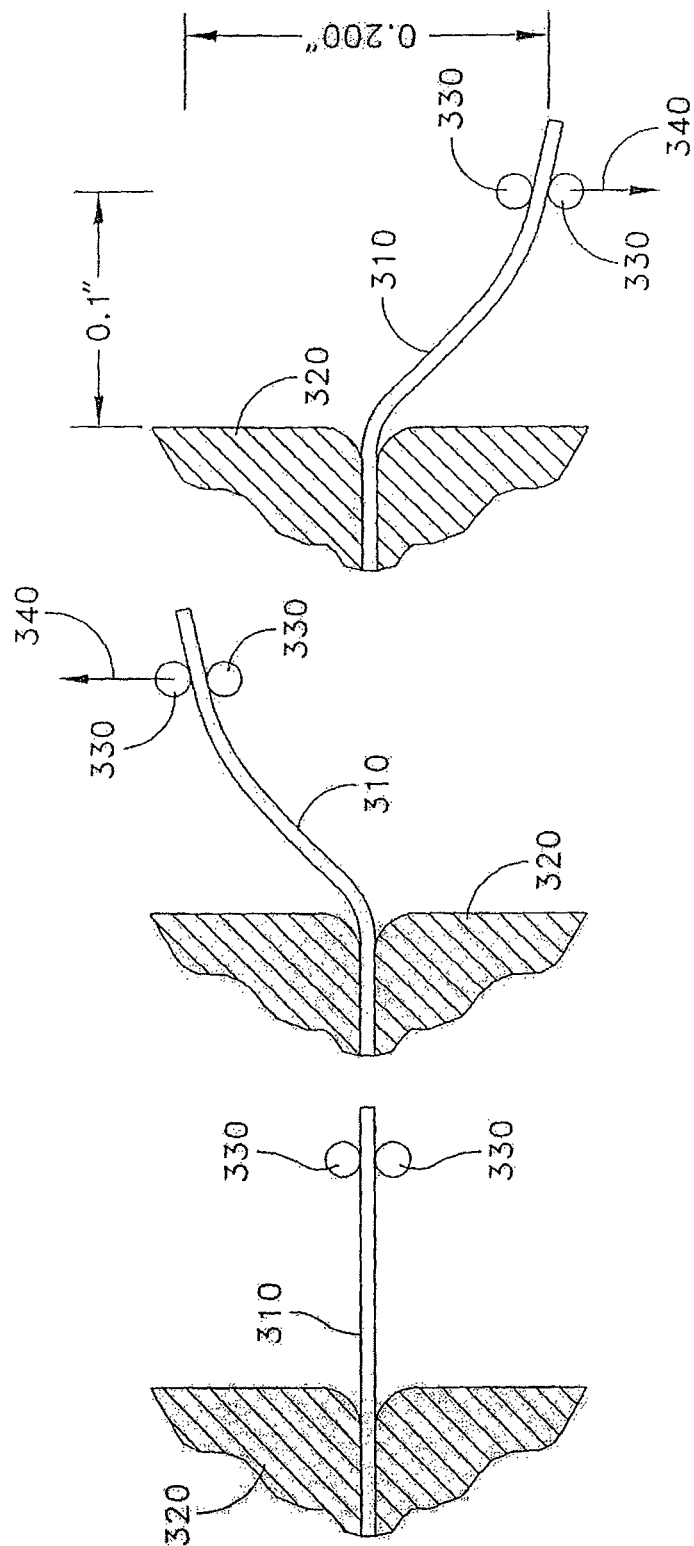
FIGS. 10A-10C show an apparatus used fix a test that shows the material transformation occurring by cyclic bending of the Strain Induced Austenite (SIA) material.

Referring to FIGS. 8 and 9, the behavior of the material during expansion was tested, specifically, 0.020" (0.05 cm) 316LVM (low carbon vacuum melted) wire in the fully annealed condition (typical of condition and chemistry for stent material). SIA 0.020" (0.05 cm) Ni—Ti-Nib pre-strained under approximately 302 ksi (2082 MPa) during a cooling cycle from 20"C to −140"C. The wire had about 10% retained strain after returning to room temperature.

Referring to FIG. 8, the testing apparatus 210 comprised two small Delran blocks 212 and 214 which were devised to hold two 0.020" (0.05 cm) wires 216 and 218 in a parallel starting configuration (wire spacing 0.100" (0.254 cm)). The spacing 220 between blocks 212 and 214 used to clamp the parallel wires 216 and 218 was about 1.414" (3.59 cm). An Instron 5544 equipped with a 20 lb (9.072 kg) load cell and Blue software was used for data capture. Specially designed micro-lifting hooks 222 and 224 (0.080" or 0.203 cm width) were designed to expand the parallel wires by hooking to the mid point of the 1.414" (3.59 cm) span and then traveling a total distance of 1" (2.54 cm) at a rate of 0.25 inch per minute C/min) (0.635 centimeter per minute (cm/min) while recording the load. Once the crosshead reached a travel distance of 1" (2.54 cm), the expanded structure was unloaded until the crosshead reached a travel distance of 0.96" (2.44 cm).

As shown in FIG. 9, the load deflection behavior of 0.020" (0.05 cm) Ni—Ti—Ni wire has compared with the 31.6LVM fully annealed wire of equivalent cross section. The "unlocking mechanism" of the Strain Induced Austenite (SIA) material was plainly visible (fine jagged pattern) in the extension range from about 1" (0.254 cm) to 0.7" (1.8 cm). In this range there was negligible force increase. The resistance to bending of the 0.020" (0.05 cm) SIA was less than half that of the 0.020" (0.05 cm) 316LVM fully annealed material. It is quite well known that 316LVM in the fully annealed condition has a yield strength of approximately 45,000 psi (310 MPa) and this would lead us to state that the yield point of the SIA material on the first cycle was considerably less than 316LVM, which is already an extremely soft ductile material. This curve also shows that the work required to achieve a given displacement was considerably reduced to achieve a given displacement when compared with 316LVM fully annealed material. After expansion to 1' (2.54 cm), the curves were unloaded to 0.96" (2.43 cm) and the load was recorded. During unloading the slope of the spring back was calculated and it was found that the 0.020" (0.05 cm) SIA material was 9.058 pounds per inch (lb/in) (1.411 newtons per millimeter (N/mm) while the 316LVM fully annealed material was 16.6 lbs/in (2.907 N/mm).

Example 6

Material Transformation Through Bending of the SIA Material

Referring to FIGS. 10A-10C and 11, a test was constructed to show the material transformation occurring by bending of the SIA material.

SIA –0.020" (0.05 cm) Ni—Ti—Nb pre-strained under approximately 302 ksi (2082 MPa) during a cooling cycle from 20° C. to –140° C. The wire had about 10% retained strain after returning to room temperature.

A straight length of 0.020" (0.05 cm) SIA material specimen 310 was clamped in mounting blocks 320 at one end and at a distance of 0.20" (0.5 cm) from the fixed end, a close fitting guide 330 machined from a plate (0.080" or 0.2 cm width) was attached. The close fitting guide 330 was attached to the crosshead 340 of an Instron 5544 equipped with a 20 lb (9.072 kg) load cell and Blue Hill software for data capture. Using the crosshead extension, the test began at the neutral position "A" (zero deflection with zero load). The cross head cycled upward +0.1" (–0.25 cm) to position "B" and downwards –0.2" (–0.51 cm) to Position "C" and then upward +0.2" (+0.51 cm) to Position "B" and so forth until the test was completed. The cross head speed was 0.2"/min or about 0.5 cm/min.

Figure 11:
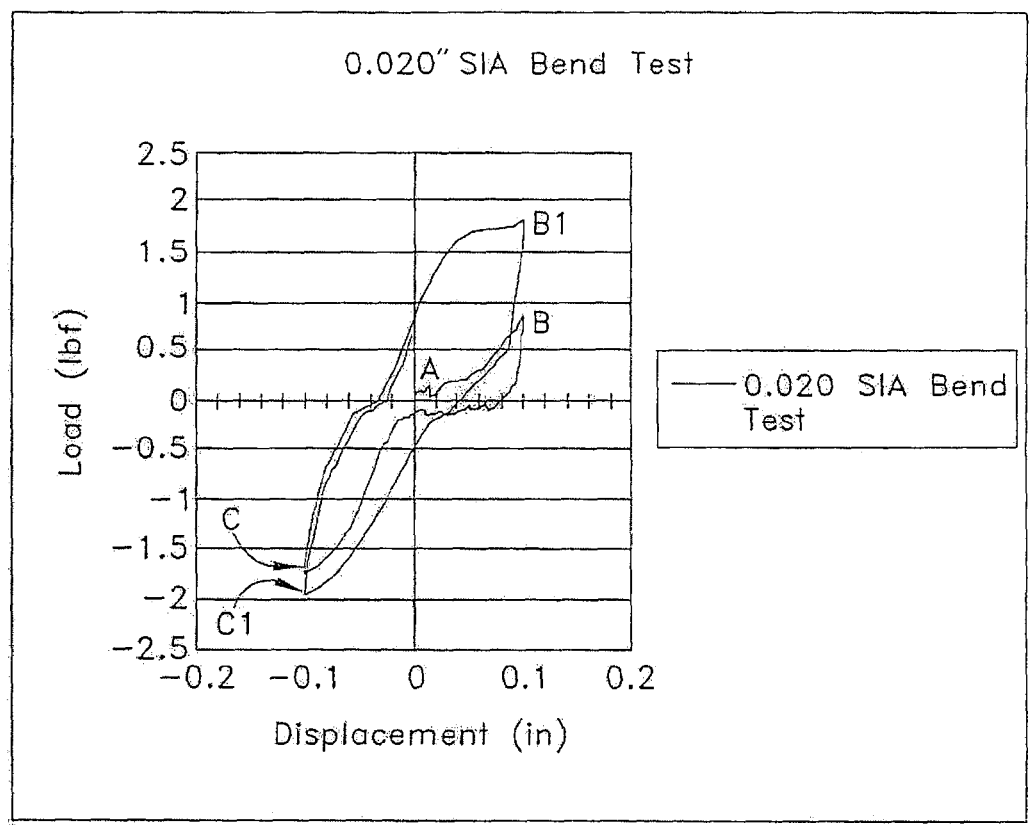
FIG. 11 is graph of the data using the apparatus in FIGS. 10A-10C.

As shown in FIG. 11, start at (A) and progress along with low force with evidence of "unlocking" to (Point B). The material was bent in the reverse direction from (Pt B) to (Pt A) with no force (more unlocking) until it got back slightly past the origin at (Pt A). Continued bending towards (Pt C) caused rapidly increasing stiffness with the force at (Pt C) more than twice the force at (Pt B). During the second round trip to Pt B1 and Pt C1, the results confirmed the material transformation was completed, demonstrating that mechanical bending converted $A_s'$ to $A_s$ for this material system (i.e., Process II of Table I). The details are discussed below.

The results in FIG. 11 show the load deflection behavior of 0.020" (0.19 cm) SIA wire for negative and positive bending conditions.

Displacement A→B

The test began at Position A (zero deflection and load). During positive bending to Position B, there was evidence of the "unlocking mechanism" at about 0.02" (0.5 cm) when the load was reduced to near zero level (shown by a large instantaneous spike). The load recovered and overall stiffness remained relatively low as the displacement increased to about 0.07" (0.17 cm) at which point the stiffness increased quickly.

Displacement B→C

During unloading, the load reduced quickly to a displacement of 0.075" (0.19 cm) as would be expected. Beyond this range, there was evidence of additional material "unlocking" as the specimen bent easily without resistance and with near zero stiffness in the displacement range of 0.07" (0.18 cm)→0.01" (0.0254 cm). At the displacement of –0.01" (0.0254 cm), the "unlocking mechanism" appeared complete, and the specimen has now transformed into a much stiffer material as evidence by the increasing load at displacement Position C.

Displacement C→B1

The material has been completely transformed and the load at B1 has increased by more than twice when compared with Position B. Additionally, in the displacement range from 0.0" (0 cm)→0.05" (0.127 cm), the load during the second cycle was four (4) to six (6) times greater than on the first cycle. This material test shows that a stiffness transformation has occurred and the "unlocking phenomena" observed in the first displacement cycle has disappeared.

Displacement B1→C1→A

Subsequent cycling shows the material is no longer exhibiting the "unlocking" phenomena and bent with considerably more stiffness than during the first cycle.

This type of curve certainly demonstrates that mechanical bending converted $A_s'$ to $A_s$ for this material system (i.e., Process II of Table I). The near zero stiffness during bending, followed by a transformation to a significantly stiffer wire is unique, and offers the potential to engineer many useful devices.

A further advantage of the present disclosure is to provide a thermal mechanical treatment regime such that $A_s'$ is sufficiently >37° C., such that little or no heat induced shape memory recovery occurs during temperature exposures caused by placement of the stent into the human body, curing of drug coatings, sterilization or shipping of finished medical devices.

In another aspect of the disclosure, it is possible to deploy a highly elastic (super-elastic) stent without having to constrain and de-constrain stress induced martensitic stent structure in contrast to, for example, Jervis, U.S. Pat. No. 5,067, 957, discussed above. In this aspect of the disclosure, a Ni—Ti-E material (as described above) having appropriate chemistry to yield a fully annealed temperature $A_s$ about –15°

C. and ideally processed to have super-elastic properties at body temperature (particularly having an "active" $A_f$ between 10° C. and 20° C.) can be "locked" by the thermal mechanical treatment means such that $A_s'>37°$ C. When placed in the human body without constraint and subsequently balloon expanded, the structure can "unlock" at which point $A_f'$ again approaches $A_f$. Applying the straining techniques above, such a material's $A_s$ could be shifted higher and the resulting structure would be martensite at body temperature. At this point, insertion into the body followed by the controlled deformation would be sufficient to restore the original $A_s$ and therefore the superelastic properties at room temperature. This alternate deployment method eliminates the force required to hold the stent in the collapsed state, reduces high friction loads between the stent and delivery sheath and minimizes the stent delivery profile.

By reverting the material back to austenite (as $A_s' \rightarrow A_s$), the superelastic Ni—Ti-E properties are reached at a certain point and then it can be further expanded easily when needed—a property particularly desirable for stent material. Furthermore, the material would possess the advantages of radiopacity and higher strength when compared to binary NITINOL.

Figure 12:
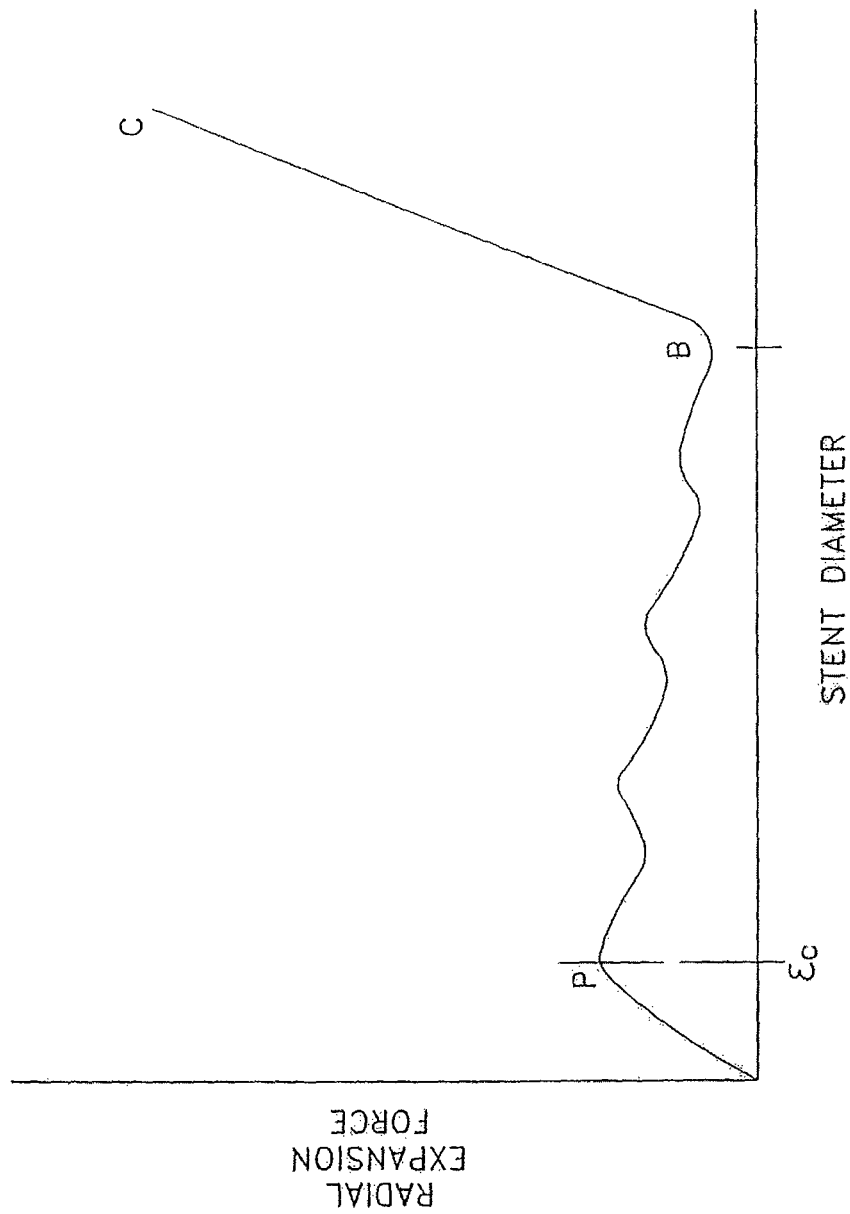
FIG. 12 is a graph showing stent diameter vs. radial expansion of a stent prepared from the strain induced austenite.

A stent fabricated from "strain induced austenite" as described in this disclosure can have a much different stent radial deployment force than those of other alloys or superelastic NITINOL. Referring to FIG. 12, initially the stent radial expansion force increases in a linear reversible fashion with stent diameter and corresponds to the elastic deformation limit of martensite along the path from the origin→P. The radial force required to achieve point P is much less than what is required to achieve the yield point of other materials (316L and Co—Cr). This is a particular advantage of the current disclosure. The "unlocking" process of martensite begins at point P and ends at point B. As the stent diameter increases, the required radial outward force is constant or decreasing during the "unlocking" process P→B where the material completes a reverse transformation to austenite.

Advantageously, when the diameter of the "unlocked" stent is sized appropriately to the vessel lumen (this would correspond to point B in FIG. 12), then no overexpansion of the lumen is required, and thus vessel trauma is eliminated or minimized. Furthermore if the vessel wall tries to contract or collapse, the stent offers a reserve of radial resistive force, as shown FIG. 13, IV. The reserve of radial resistance is coming from the material transformation of martensite to austenite by the controlled deformation of the stent expansion cycle. The change in material stiffness is shown by examining FIG. 5 SIA—subsequent bending cycle.

In the present disclosure, the force required to reach the fully deployed stent diameter (point B FIG. 12) can be much less than the expansion force required by a stent made from other materials. The reduced expansion force can lead to an optimization of the stent delivery profile.

Biomedical Device Applications

In general, systems using the present material can provide higher mechanical properties than other binary alloys (for example, NITINOL, resulting in smaller device cross sections and minimal design profile. Such devices can reduce trauma since they do not have to be overdeformed during deployment, as in the case of materials such as stainless steel (316L), Co—Cr alloys (L605, MP35N), and titanium-based materials. Another advantage of the present materials is less inflation pressure of the balloon. The addition of Nb or Ta into the Ni—Ti-E alloy can improve the radio-opaque properties of the material, allowing doctors to find the location of smaller cross sections under X-Ray fluoroscopy. The alloy exhibits nonmagnetic, low torque properties, and offers a crisp image under MRI imaging which is a medically desirable property.

For percutaneous, intraluminal and laproscopic medical device applications, the present disclosure offers multiple advantages including: very low deployment forces, delivery systems with more flexible and smaller cross sections, and inflation balloons with thinner cross sections and lower operating pressures for safer and higher reliability. Designs using the present material do not have to be held in the compressed position awaiting deployment, such as binary NITINOL at high stress levels (>60 ksi or 413 MPa) during shipping, sterilization and storage.

Stents and Stent Grafts

As discussed above, stents are fabricated from laser cut tubes, braided, coiled or formed wires fabricated into tubular structures and used to repair the patency of narrowed, previously weakened or ballooned and otherwise impaired lumen or other body channels. They are deployed by the use of catheters in percutaneous, intraluminal or laproscopic procedures. Examples are: blood vessels, bile duct, esophagus, urethra, trachea and the like. Specifically: carotid and coronary vessel, intraluminal lining of aortic abdominal aneurysms, iliac or femoral aneurysms, recanalization of injured vessels caused by blunt or penetrating trauma, dilation and recanalization of stenotic arterial segments, tampanade and obliteration of esophageal varices, recanalization of esophageal stenoses secondary to carcinoma or benign strictures, ureteral strictures and tracheal strictures. In all these applications, the present shape memory alloy would be advantageous in its ease of deployment.

The present disclosure improves on the current state of the art in several ways and the specific advantages depend upon the base material system in the comparison.

For example, the present disclosure improves over a NITINOL stent by having little or no outward radial force when placed in the delivery system tube. A binary NITINOL stent exerts a chronic outward force on the inside wall of the delivery system, and during storage the inside watt of the delivery system sheath may become imprinted by the stent frame. During deployment of the NITINOL stent, the frictional forces may be quite high, whereas devices formed from the present alloys deploy more easily and provide a more flexible and reduced delivery sheath cross-section. Furthermore, after the expansion of a stent made from the present alloys is expanded, and the transformation described herein is complete, the new material can provide stiffer characteristics than, for example, binary alloys such as NITINOL. A further advantage is that niobium is very radiopaque under x-ray fluoroscopy whereas NITINOL is not.

When compared with a 316L stent, the present disclosure reduces the delivery system profile, the balloon expansion pressure is reduced and the total amount of work required to deploy the stent system is also reduced. The expansion force of a 316L stent increases linearly as the stent diameter is expanded while the present disclosure can achieve significant stent expansion at near zero force as the diameter expands. The lower expansion force characteristic leads to a reduced cross section of the balloon inflation catheter, thereby leading to a lower profile and improved flexibility for the delivery system. A further advantage is that niobium is very radiopaque under X-ray fluoroscopy, whereas 316L is considered to have poor visibility.

Figure 13:
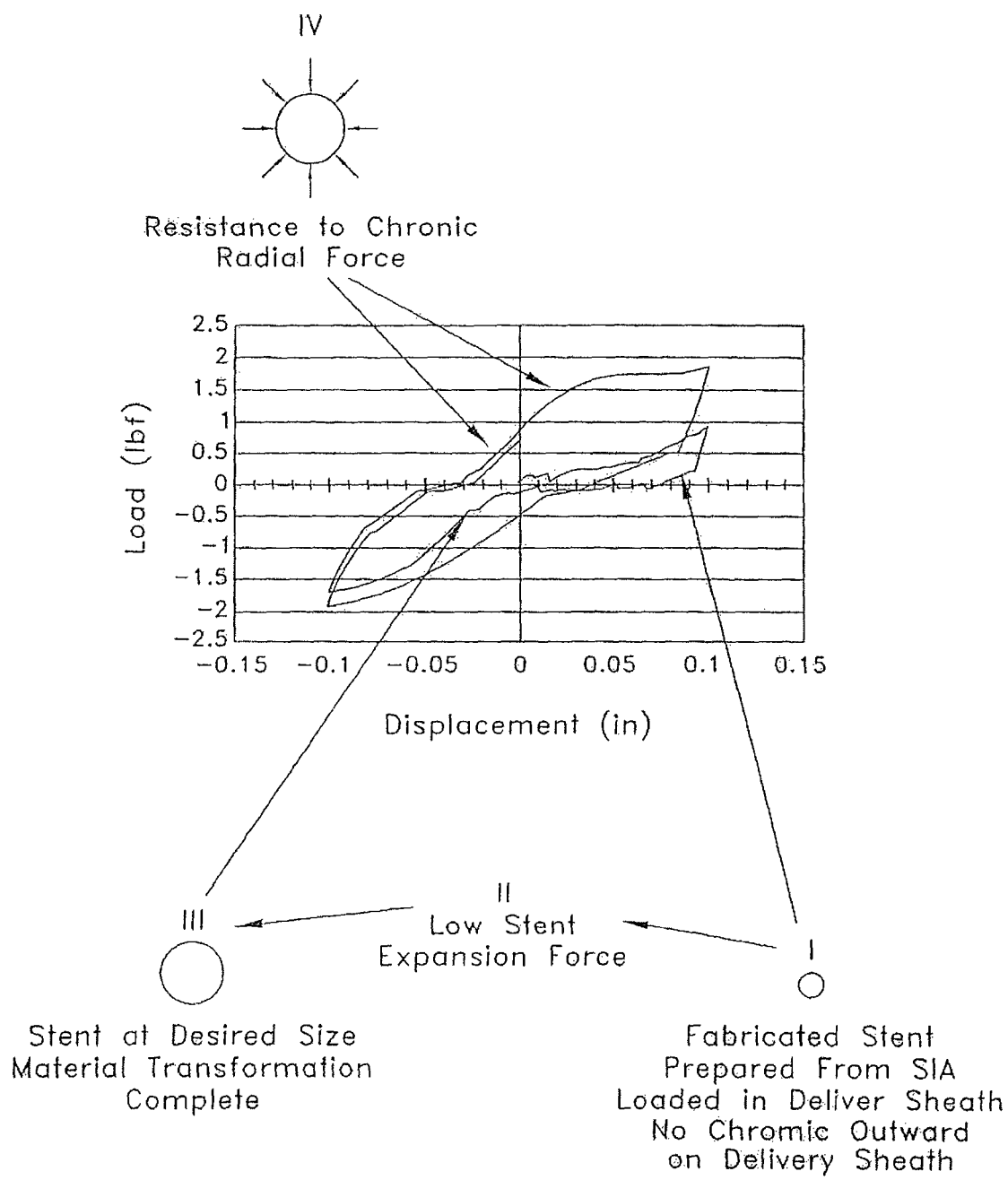
FIG. 13 shows the strain behavior for a stent fabricated from strain induced austenite in relation to FIG. 11.

FIG. 13 is an example of how a stent fabricated from strain induced austenite works overlaid with the data from FIG. 11. The displacement axis represents a small about of bending taking place in the struts of individual stent cells. These tiny stent cell displacements could also represent changes in stent diameter. Roman Numerals I that IV show the stent deployment relative to the material properties. Therefore, I shows a prepared stent loaded into the delivery system, II shows the near zero deployment and expansion force, III shows the fully expanded stent at the location of complete material transformation, and IV shows how the transformed stent material can now provide resistance to chronic radial force.

Surgical Staples

Surgical staples are typically made from 316L and titanium wire having been formed and loaded into delivery magazines. In many applications, a delivery magazine can hold 100 or more staples and they can be simultaneously fired at once. It is desirable to lower the combined firing force to push multiple staples from the magazine holder and simultaneously crimp the wire staples into the traditional B-shape profile.

The present application can improve upon multiple staple tiring systems by reducing the total work and maximum force required to deploy a given number of staples and compress those staples into the required B-shaped profile. The initial low stiffness of the present disclosure allows engineers to redesign either: (a) surgical staple devices that are easier for the physician to grasp and tire, or (b) allow engineers to design surgical staple guns that fire more staples for an equivalent grasping force.

Medical Expansion Bolt/Bulkhead Connector Applications it is also possible to utilize the strain induced austenite disclosure to design and fabricate a device that can fit through a small blind hole. Once inserted and mechanically expanded, the device can take on the new structural shape of a particular design intent that can prevent its removal. One particular application is the Vascular Hole Closure device in which a vessel wall is sealed from the outside wall. This can be achieved by inserting a device comprising the material into the vessel hole (resulting from a previous medical procedure) and causing a controlled deformation deployment means expanding the device in such a way that it cannot be removed, and thereby seals the hole. A second similar application in which the material may be useful is the atrial septal defect device.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. A method for the thermal mechanical treatment of a shape memory ternary alloy, said alloy comprising a third insoluble alloying element, said method performed at temperatures $<M_d$ wherein the hysteresis is widened such that after the treatment is completed $A_s<A_s'$ comprising:
    a) annealing or partially annealing a shape memory alloy through a high temperature solution treatment followed by cooling;
    b) mechanically straining the alloy under a load while simultaneously cooling the material to a temperature around $M_s$, to produce locked martensite thus widening the hysteresis such that $A_s<A_s'$ and retaining a sufficient amount of strain in the strained element whereby if controlled deformation is applied the alloy is transformed to the austenitic phase, shifting $A_s'$ to $A_s$ by unlocking the martensite; and
    c) applying controlled deformation sufficient to initiate the unlocking of martensite whereby the alloy is transformed to austenite wherein $A_s'$ is shifted to $A_s$.

2. A method for manufacturing a medical device for use in a body lumen, comprising:
    forming a structural element from the alloy manufactured by the method of claim 1 into a desired medical device geometry which includes a hollow structure comprising a mesh like pattern having struts and nodes, the structural element being capable of assuming a first position, a second position and a third position wherein the first position, the alloy has been processed in an austenitic phase and wherein a second position the alloy of the first position is cooled and mechanically collapsed for deployment into the body lumen, the nodes achieve high levels of straining which can be retained in the collapsed second position as locked martensite and, wherein the third position is achieved after controlled deformation is applied to mechanically expand the hollow structure thereby releasing the retained strain to transform the locked martensite nodes into austenite, enhancing the structure's ability to resist radial loads.

3. The method according to claim 2, wherein the alloy is Ni—Ti.

4. The method according to claim 2 wherein while mechanically collapsing the structure such that the nodes are strained between about 4% and 25% under a sufficient load while simultaneously cooling the material to a temperature to approximately $M_s$, thus shifting the $A_s$ of the highly strained nodes up higher such that $A_s<A_s'$ and retaining about 2% to about 16% strain in the nodes whereby if controlled deformation is applied the nodes will transform to the austenite, shifting the nodes transformation property from $A_s'$ to $A_s$.

5. The method according to claim 4, whereby the structural element incorporates collapsing of the structural element for deployment and the pre-straining of nodes into a single process step.

6. The method according to claim 5, whereby the structural element is mechanically expanded and nodes are mechanically transformed by the expansion process from $A_s'$ to $A_s$.

7. The method of claim 2 whereby the alloy of the second position is stable for insertion into the body lumen without a restraining cover and $A_s'>$body temperature.

8. A method for manufacturing a medical device for use in a body lumen, comprising:
    forming a structural element from the alloy manufactured by the method of claim 1 into a desired medical stent device geometry which includes a hollow structure, the structural stent element having a plurality of stent cells and said element being capable of assuming a first position and a second position wherein in the first position, the alloy has been processed in an austenitic phase and wherein in the second position, the alloy of the first position is cooled and mechanically collapsed for deployment into the body lumen, and comprises high levels of strain in the stent cells which is retained in the collapsed second position as locked martensite, wherein after controlled deformation is applied to mechanically expand the hollow stent structure thereby releasing the retained strain, transforming the locked martensite into austenite, enhancing the structure's ability to resist radial loads.

9. The method according to claim 8, wherein the alloy is Ni—Ti.

10. The method according to claim 8 wherein while mechanically collapsing the structure such that the stent cells when collapsed are strained between about 4% and 25% under a sufficient load while simultaneously cooling the material to a temperature to approximately $M_s$, thus shifting the $A_s$ of the highly strained stent cells up higher such that $A_s < A_s'$ and retaining about 2% to about 16% strain in the stent cells whereby if controlled deformation is applied, the stent cells will transform to the austenite, shifting the stent cells transformation property from $A_s'$ to $A_s$.

11. The method of claim 8 whereby the alloy of the second position is stable for insertion into the body lumen without a restraining cover and $A_s'$ > body temperature.

* * * * *